(12) United States Patent  
Hotokebuchi et al.

(10) Patent No.: US 8,400,312 B2
(45) Date of Patent: Mar. 19, 2013

(54) OPERATION ASSISTING SYSTEM

(75) Inventors: Takao Hotokebuchi, Saga (JP); Kenbu Teramoto, Saga (JP); Masamori Shigematsu, Saga (JP)

(73) Assignee: Saga University, Saga (JP)

( * ) Notice: Subject to any disclaimer, the term of this patent is extended or adjusted under 35 U.S.C. 154(b) by 726 days.

(21) Appl. No.: 12/311,531

(22) PCT Filed: Oct. 9, 2007

(86) PCT No.: PCT/JP2007/069684
§ 371 (c)(1),
(2), (4) Date: Jan. 21, 2010

(87) PCT Pub. No.: WO2008/044679
PCT Pub. Date: Apr. 17, 2008

(65) Prior Publication Data
US 2010/0127879 A1    May 27, 2010

(30) Foreign Application Priority Data

Oct. 10, 2006 (JP) .................. 2006-276384

(51) Int. Cl.
*A61F 2/32* (2006.01)
*A61F 2/36* (2006.01)
*A61F 2/30* (2006.01)
*A61B 5/05* (2006.01)
*A61B 5/103* (2006.01)
*G08B 23/00* (2006.01)
*G08B 1/08* (2006.01)

(52) U.S. Cl. ............... 340/573.7; 623/22.15; 623/22.12; 623/23.22; 623/22.11; 623/18.11; 600/424; 600/587; 600/426; 340/539.12

(58) Field of Classification Search ............... 340/573.7, 340/539.12; 623/22.15, 22.12, 23, 22.11, 623/66, 18.11; 600/424, 587, 426; 128/898
See application file for complete search history.

(56) References Cited

U.S. PATENT DOCUMENTS

| | | | | |
|---|---|---|---|---|
| 5,007,936 A | * | 4/1991 | Woolson | 128/898 |
| 5,127,920 A | * | 7/1992 | MacArthur | 623/22.11 |
| 6,711,431 B2 | * | 3/2004 | Sarin et al. | 600/426 |
| 6,991,655 B2 | * | 1/2006 | Iversen | 623/22.12 |
| 7,001,346 B2 | * | 2/2006 | White | 600/587 |

(Continued)

FOREIGN PATENT DOCUMENTS

| | | |
|---|---|---|
| JP | 2002-085421 | 3/2002 |
| JP | 2004-237101 | 8/2004 |

(Continued)

OTHER PUBLICATIONS

International Search Report (Form PCT/ISA/210); Internationla Application No. PCT/JP2007/069684; Dated: Jan. 7, 2007.

*Primary Examiner* — Jennifer Mehmood
*Assistant Examiner* — Mirza Alam
(74) *Attorney, Agent, or Firm* — Rader, Fishman & Grauer PLLC

(57) ABSTRACT

An operation assisting system. When an operator manipulates an operation instrument to perform an operation for a joint surgery including a hip replacement, the operation assisting system provides the operator with information on the orientation of a bone such as a pelvis and an appropriate direction of the operation instrument relative to the bone to assist the operator so as to complete the operation in an easy and accurate manner, which ensures a high degree of operation accuracy and reduces the cost of the system.

20 Claims, 8 Drawing Sheets

U.S. PATENT DOCUMENTS

| | | |
|---|---|---|
| 7,594,933 B2 * | 9/2009 | Kammerzell et al. ..... 623/22.15 |
| 2003/0181830 A1 * | 9/2003 | Guimond et al. ............. 600/587 |
| 2004/0092944 A1 * | 5/2004 | Penenberg ...................... 606/91 |
| 2004/0230199 A1 * | 11/2004 | Jansen et al. .................... 606/91 |
| 2005/0065617 A1 * | 3/2005 | Moctezuma de la Barrera et al. ........ 623/908 |
| 2009/0316967 A1 * | 12/2009 | Dardenne et al. ............. 382/128 |

FOREIGN PATENT DOCUMENTS

| | | |
|---|---|---|
| JP | 2005-030911 | 2/2005 |
| JP | 2005-137904 | 6/2005 |
| JP | 2006-263241 | 10/2006 |
| JP | 2005-224613 | 8/2008 |
| WO | WO 2004/112610 A2 | 12/2004 |
| WO | WO 2005/104783 A2 | 11/2005 |

\* cited by examiner

OPERATION ASSISTING SYSTEM

TECHNICAL FIELD

The present invention relates to an operation assisting system, which permits to provide, when an operator manipulates an operation instrument to perform an operation for a joint surgery including a hip replacement, the operator with information on orientation of a bone such as a pelvis and an appropriate direction of the operation instrument relative to the bone to assist the operator so as to complete the operation in an easy and accurate manner, and particularly to such an operation assisting system, which permits to ensure a high degree of operation accuracy and reduce costs of the system.

BACKGROUND OF THE INVENTION

In a hip replacement coping with a hip osteoarthritis, parts for forming a prosthetic joint are substituted for a caput femoris and an acetabuli of a pelvis, respectively. An operation for the hip osteoarthritis includes removing partially the caput femoris and the acetabuli, and then implanting the parts substituting for the removed portions thereof. Such an operation, which has an influence on a range of movement of a hip joint after completion of the operation, should be performed in an accurate manner.

According to a conventional operation, medical physicians utilize a photograph of an X-ray photography or a fluoroscopy thereof to provide an illustration of a bone, confirm a positional relationship of the bone, and then determine a site of a body to which operation instruments such as an impactor are to be applied and a way of operation based on a body trunk of a patient, which can be obtained through a visual measurement by the medical physicians, by their experiences and intuition, thus advancing the operation.

Even if the experienced operators may acquire an interrelationship between the bone and the operation instruments with a high degree of accuracy to manipulate appropriately the operation instruments in a manner as described above, there is however a high risk that the body of the patient may unexpectedly move. In case where the bone deviates from its original ideal position as set, the operation based on the visual measurement may not cope with even a slight deviation in an operational condition in which an existence of an operation cloth usually disables the operators from directly observing the entire hip of the patient. This makes it not possible to ensure an accuracy of the operation, thus causing problems that a range of movement of the hip joint after completion of the operation may become narrower or a bone dislocation may easily occur.

In view of these problems, there has recently been proposed an operation navigation system in which, three-dimensional spatial data of a bone including a site on which an operation is to be performed are previously prepared from images obtained through a CT scan or an MRI prior to the operation, infrared markers provided on the surface of the body of the patient in the vicinity of the site on which the operation is to be performed and on an operation instrument and a related infrared positional measurement device are used to acquire the positions of the infrared markers during the operation to obtain the spatial positions the bone and the operation instrument, and the thus obtained spatial positions and the direction of the bone are compared with the three-dimensional spatial data of the bone to determine accurate position and direction of the site such as a joint on which the operation is to be performed, and then the operator is navigated with an accurate information on a manipulating direction of the operation instrument relative to the site on which the operation is to be performed, through a laser pointer or a display unit.

For example, Japanese Patent Provisional Publication No. 2002-85421 and Japanese Patent Provisional Publication No. 2005-30911 describe such a conventional operation assisting system.

The above-described conventional operation navigation system gives instructions on a position toward which the operation instrument is moved and a direction along which the operation instrument is directed on the display unit to provide a way, which enables the operation to be performed accurately irrespective of movement of the site on which the operation is to be performed.

Patent Document 1: Japanese Patent Provisional Publication No. 2002-85421
Patent Document 2: Japanese Patent Provisional Publication No. 2005-30911

DISCLOSURE OF THE INVENTION

Subject to be Solved by the Invention

The conventional operation navigation system, which has the configuration as disclosed in the respective patent documents as identified above, permits to effectively assist steps such as a step of implanting joint parts by the operator on a basis of a visual guidance. However, use of material such as the infrared markers, which require an optical detection, it is necessary to provide, in addition to the markers provided on the surface of the body of the patient and on the operation instrument, a positional measurement device to acquire optically the positions of the markers in an operation room, thus causing a problem of extraordinary costs as required for installing and operating this system. A certain place at which the operator or assistant operates may disable the positional measurement device from directly monitoring the markers during the operation, with the result that the positions of the markers may not be acquired accurately, thus deteriorating accuracy of positional detection.

An object of the present invention, which has been made to solve the above-described problems is therefore to provide an operation assisting system, which utilizes a sensor that is provided, in a vicinity of a site on which an operation is to be performed, so as to be capable of acquiring independently positional information, and which system permits to acquire accurately a state of the site on which the operation is to be performed, without being affected by surroundings, to manipulate appropriately an operation instrument and perform the operation on a joint of a bone in an easy and accurate manner, and simplify a mechanism of detecting the site on which the operation is to be performed and a position of the operation instrument with the use of the sensor, thus ensuring a high degree of operation accuracy and reducing the costs for the general system.

Means to Solve the Problems

An operation assisting system according to the present invention comprises: radiopaque markers provided at predetermined points on a surface of a body of a patient, who is to be held in a predetermined operational posture on an operating table kept in a fixed position, the predetermined points being placed in a vicinity of a bone of the patient, which is to be subjected to an operation, and having respective constant positional relationships relative to the bone, the radiopaque markers having constant positional relationships to each other; a sensor provided at a predetermined point on the surface of the body of the patient so as to have a constant positional relationship relative to the markers, the sensor being configured to detect at least inclination of the sensor relative to an imaginary reference plane, which is kept in a fixed position together with the operating table, the sensor enabling its positional relationship relative to the bone to be acquired based on positional relationships between the bone and the respective markers, which have been previously acquired through an X-ray photography; an arithmetic control unit configured to receive a sensor output from the sensor and acquire inclination of the bone relative to the reference plane based on the inclination as detected of the sensor and the positional relationship thereof relative to the bone, as well as determine deviation between a proper inclination of the bone relative to the reference plane, which the bone should have during the operation to be performed on a site of the bone, and an actual inclination of the bone relative to the reference plane, to generate an instruction image indicative of the deviation; and a display unit configured to display the instruction image.

According to the present invention, the sensor, which is capable of acquiring inclination thereof relative to the imaginary reference plane kept in the fixed position, is provided on the surface of the body in the vicinity of the bone, with a positional relationship to the bone kept constant, to acquire appropriately inclination of the bone during the operation. This makes it possible to adjust the position of the bone to an ideal state, when performing the operation in which an operation instrument must accurately reach the site of the bone on which the operation is to be performed, and to handle always the operation instrument by a certain operation as set to improve an operation accuracy, thus ensuring improvement in function of the site after completion of the operation. In addition, there is no need to an optical acquisition of three-dimensional position of the bone during the operation, thus solving difficulty in an appropriate positional measurement due to interception of the light for the positional measurement by the operator or assistant during the operation. There occur no problems that movement of the operator or assistant during the operation is limited by the positional measurement device, thus enabling the operator to concentrate upon performing the operation and providing an excellent operability.

The operation assisting system may further comprises: a second sensor stationarily provided at a predetermined position on an operation instrument to detect at least inclination of the second sensor relative to the reference plane, the operation instrument being placed in a vicinity of the site on which the operation is to be performed, and used through operation by an operator; and wherein: the arithmetic control unit is configured to receive a sensor output from the second sensor and acquire inclination of the operation instrument relative to the reference plane based on the inclination as detected of the second sensor, as well as determine deviation between a proper inclination of the operation instrument relative to the bone, which the operation instrument should have during the operation to be performed on the site, and an actual inclination of the operation instrument relative to the bone, to generate a second instruction image indicative of the deviation; and the display unit or another display unit is configured to display the second instruction image.

According to the present invention, the second sensor is provided on the operation instrument. This makes it possible to acquire, from the sensor input, inclination of the operation instrument relative to the reference plane, cause the arithmetic control unit to analyze the thus acquired inclination and the inclination of the bone relative to the reference plane, which is outputted from the sensor provided on the bone, to display deviation between the actual inclination of the operation instrument and the proper inclination of the operation instrument relative to the bone. Thus, the operator can manipulate the operation instrument so as to reduce the deviation, while observing the display, to cause the operation instrument to reach the site on which the operation is to be performed. An accurate operation can therefore be achieved through an appropriate guidance for the operation instrument in a simple mechanism, thus establishing a system for navigation of the operation at low costs.

The operation assisting system may further comprises: a third sensor provided at a predetermined point on the surface of the body, the predetermined point having a constant positional relationship relative to an other bone adjacent to the bone through a joint and placed in a vicinity of the other bone, to detect at least inclination of the third sensor relative to the reference plane; and wherein: the arithmetic control unit is configured to receive a sensor output from the third sensor and acquire inclination of the other bone relative to the reference plane based on the inclination as detected of the third sensor to determine inclination of the other bone relative to the bone, as well as receive, when an angle of the other bone relative to the bone in a predetermined inclination direction reaches a critical inclination angle, an angle value and the inclination direction, store the critical inclination angle in the inclination direction, accumulate the critical inclination angles in all of possible inclination directions and provide a range of movement of the joint to generate an image indicative of the range of movement; and the display unit or another display unit is configured to display the range of movement.

According to the present invention, the third sensor is provided for the other bone placed adjacently to the above-mentioned bone through the joint with the result that the sensors are provided for the respective bones. This makes it possible to acquire the inclination of the other bone relative to the reference plane from the output of the third sensor, cause the arithmetic control unit to analyze the outputs of the sensor provided for the bone and the third sensor to acquire inclination between the bones, and store and accumulate the critical inclination angles in the respective inclination directions to obtain the range of movement of the other bone relative to the bone. Therefore, the range of movement can be obtained before performing the operation to achieve establishment of an appropriate pre-operation diagnosis and an operation plan. The range of movement of the joint can accurately be obtained during the operation, thus permitting to use effectively the thus obtained information to give the patient an explanation about functions of the joint after the operation.

The operation assisting system may further comprises: an input unit being configured to enable an operator to input an instruction to the arithmetic control unit, the instruction being indicative that the inclination of the other bone relative to the bone reaches the critical inclination angle; and wherein: the arithmetic control unit is configured to store, in case where, after prosthetic joint parts are fixed to the other bone and the bone to be subject to the operation and then the prosthetic joint parts are connected to each other, the inclination of the other bone relative to the bone due to a bending operation carried out by the operator or an operation assistant at a position of the joint of a body site including the other bone of the patient reaches a critical angle of inclination without reaching a critical angle based on specifications of the prosthetic joint parts, the critical angle as the critical inclination angle in the predetermined inclination direction in accordance with an instruction input carried out thorough the input unit by the operator recognizing the critical angle of inclination as reached, as well as set, in an inclination direction at which a smooth inclination takes place to reach the critical angle based on the specifications of the prosthetic joint parts, the critical angle of the prosthetic joint parts as the critical inclination angle, accumulate the critical inclination angles in respective inclination directions and provide a range of movement of the joint between the other bone and the bone to generate an image indicative of the range of movement; and the display unit or another display unit is configured to display the range of movement.

According to the present invention, it is possible to cause the arithmetic control unit to acquire, after the prosthetic joint parts are fixed to the bones and connected to each other during the operation, an angle between the bones based on the outputs from the sensors provided for these bones between which the joint is placed, and to receive the instruction input at a critical position in the respective directions, in which a certain site of the body including the other bone of the patient actually moves relative to the other certain site of the body including the bone thereof, and accumulate-processing the data to obtain the range of movement of the joint. Therefore, it is possible to recognize during the steps of the operation a safe range of movement within which dislocation of the joint may not occur. As a result, an appropriate advice about treatment after the operation and the range of movement of the joint may be given to the patient.

The operation assisting system may be characterized in that: the arithmetic control unit is configured to output a predetermined annunciation signal, in case where the inclination of the other bone relative to the bone in the predetermined inclination direction due to a bending operation carried out after completion of the operation by an assistant at a position of the joint of a body site including the other bone of the patient, or due to a moving action of the patient based on his/her will, reaches a critical angle of inclination in the inclination direction, which has been derived from known data of the range of movement for the prosthetic joint parts as implanted; and the system may further comprise: an annunciation unit being configured to receive the annunciation signal and perform annunciation relative to the assistant and/or the patient.

According to the present invention, it is possible to cause the arithmetic control unit to acquire, after completion of the operation, the angel between the bones on the basis of the outputs from the sensors provided for the respective bones between which the joint is placed. In addition, it is possible to use the data of the range of movement as previously accumulated to perform annunciation by the annunciation unit in case where, when an assistant or the patient himself or herself actually moves a certain site of the body including the other bone of the patient relative to the other certain site of the body including the bone thereof, the angle reaches the critical angle of inclination in the respective directions. This makes it possible to cause the patient to recognize appropriately the range within which the joint can move without causing any problems. Such recognition of a safe range of movement previously given to the patient enables him/her to refrain from forcedly moving the prosthetic joint to reduce the risk of dislocation, thus providing the patient with an appropriate support for use of the joint after recovery.

The operation assisting system may be characterized in that: the bone comprises a pelvis; the markers are provided at respective vertices of a triangle on the surface of the body of the patient on a back side of a sacral bone of the pelvis; and the sensor is provided within the triangle including the markers at the vertices thereof on the back side of the sacral bone of the pelvis.

According to the present invention, in case where a predetermined site of the pelvis is set as a site on which the operation is to be performed, the sensors are provided together with three markers on the surface of the body of the patient on the back side of the sacral bone, which has substantially no influence on movement of the pelvis. This makes it possible to stationarily provide the sensors on the pelvis in a reliable manner so as to be substantially integrally connected to the pelvis. Therefore, the movement of the pelvis can be reflected surely in the sensors, thus permitting an accurate detection of the inclination of the pelvis.

Figure 1:
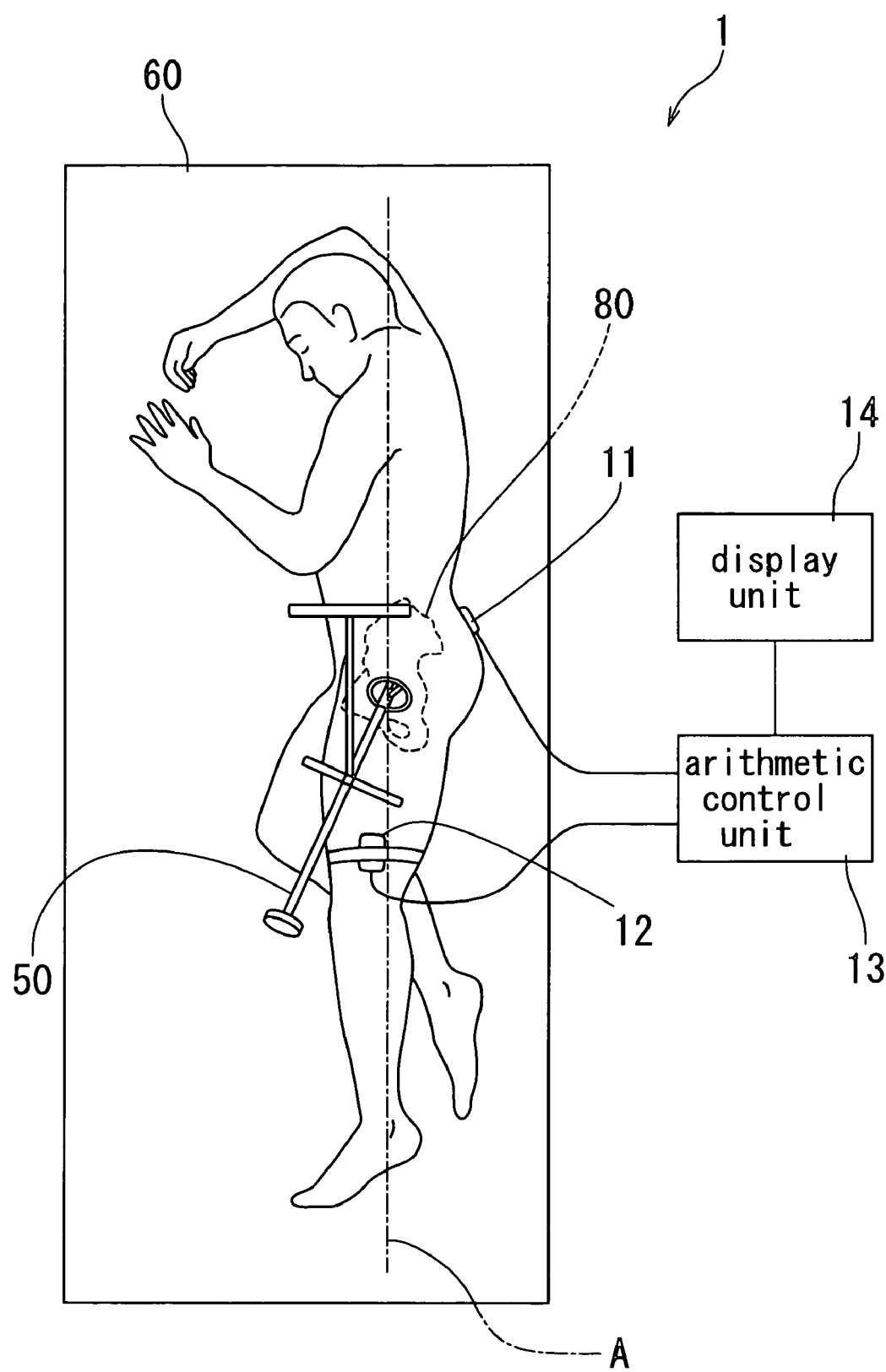
FIG. 1 is a schematic descriptive view of an operation assisting system according to the first embodiment of the present invention.
Figure 2:
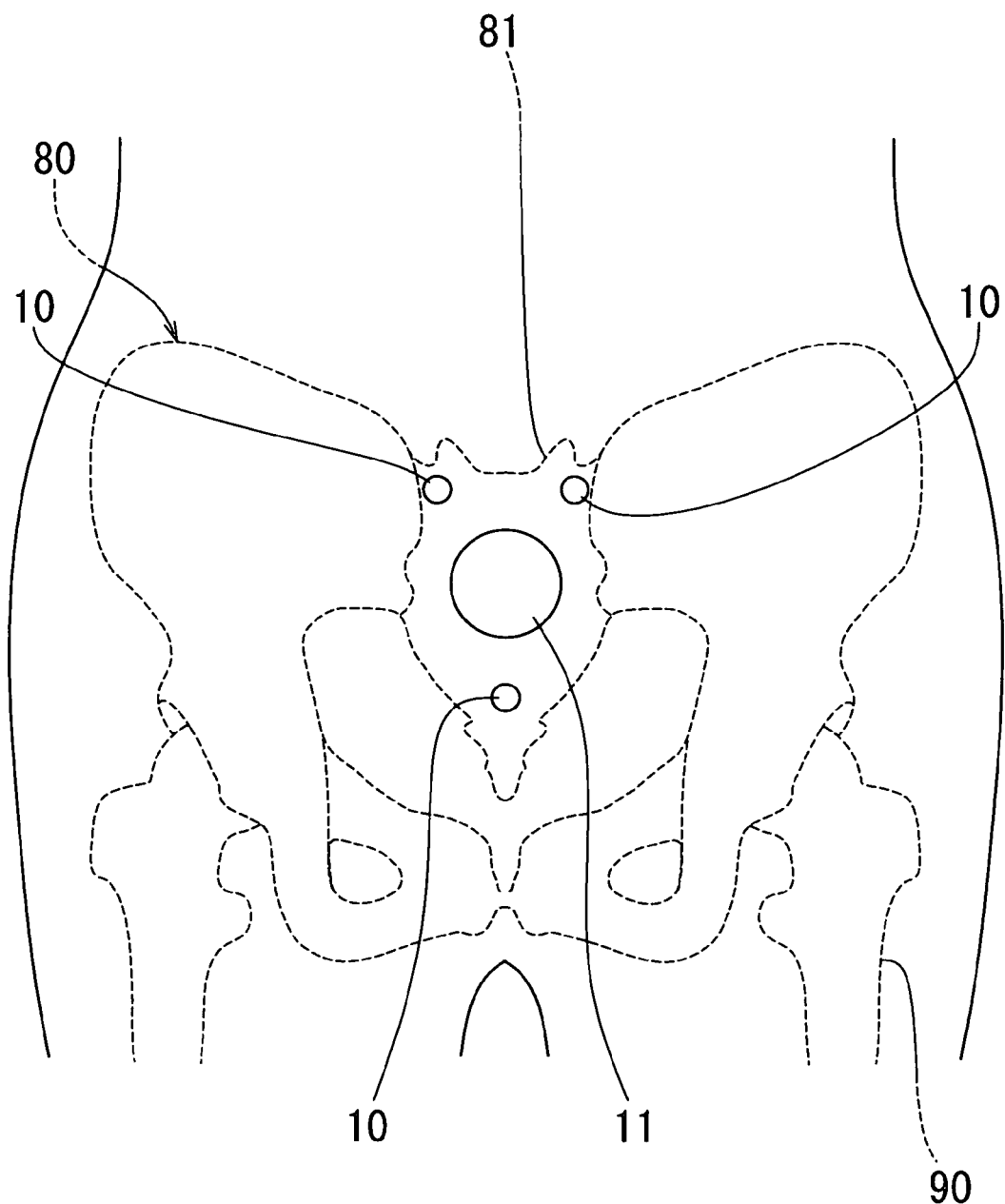
FIG. 2 is a view illustrating positions at which first sensors are provided in the operation assisting system according to the first embodiment of the present invention.
Figure 3:
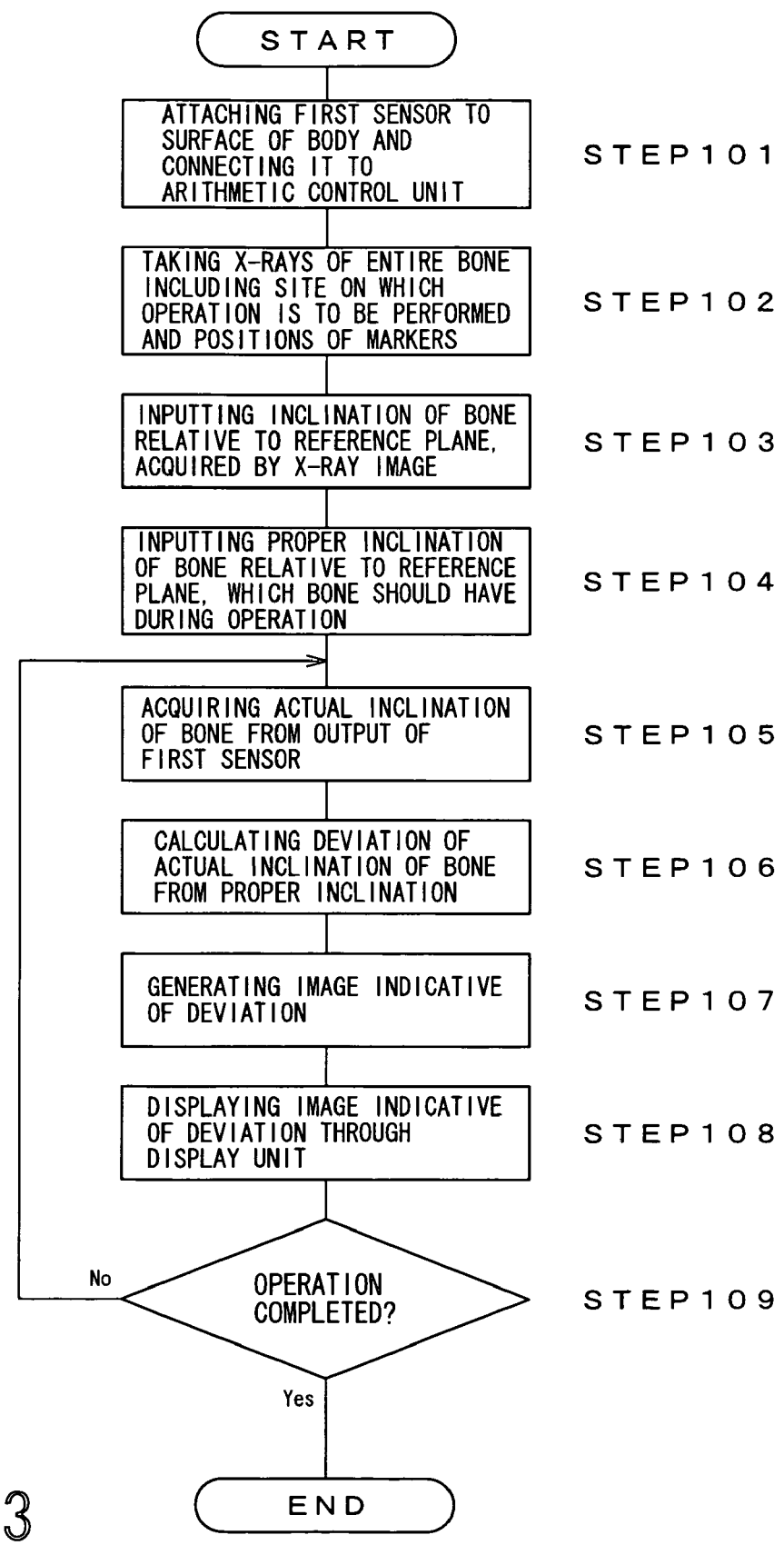
FIG. 3 is a flowchart of assisting operations in the operation assisting system according to the first embodiment of the present invention.
Figure 4:
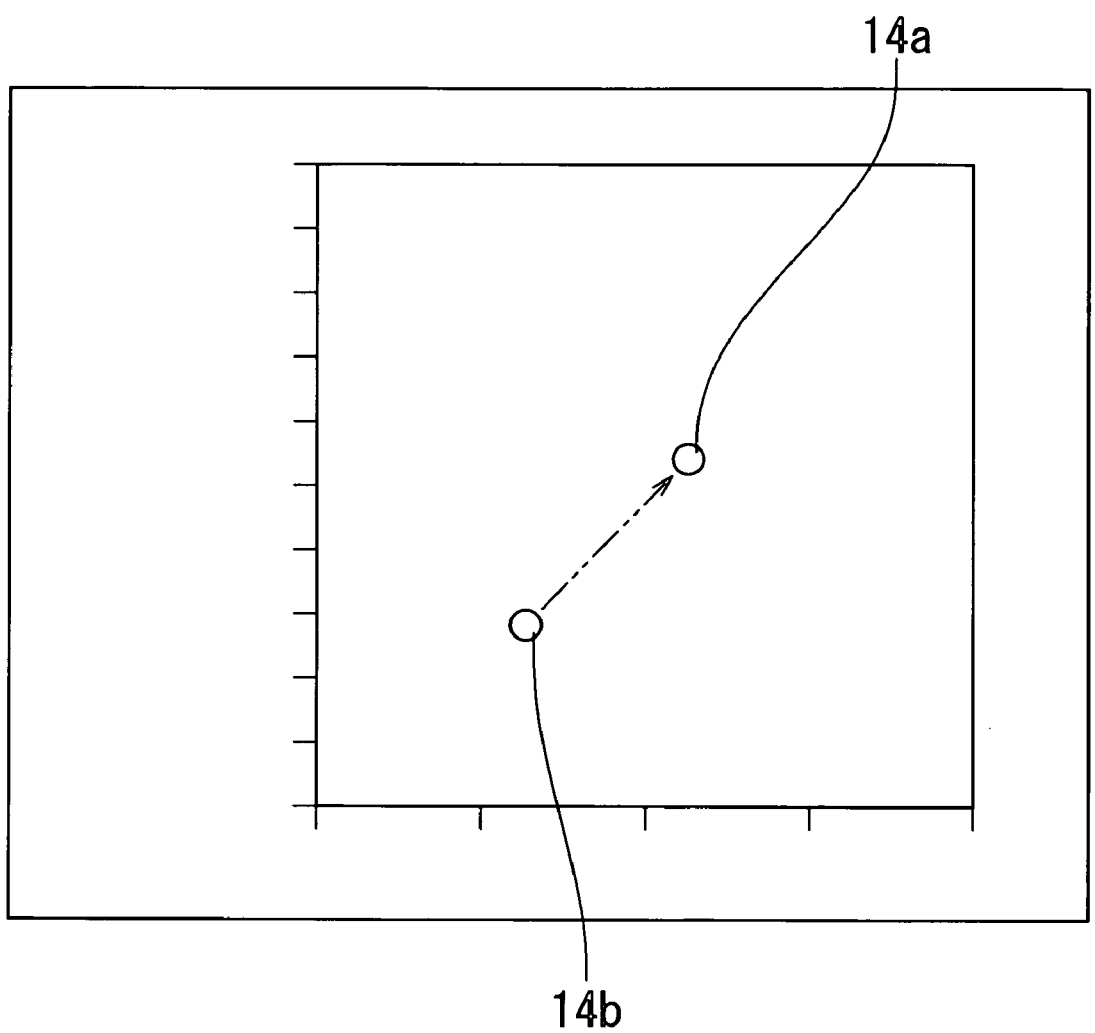
FIG. 4 is a descriptive view illustrating a screen of a display unit of the operation assisting system according to the first embodiment of the present invention.

EXPLANATION OF THE REFERENCE NUMERALS 1, 2 operation assisting system
10, 20 marker
11, 21 first sensor
12, 23 third sensor
13, 24 arithmetic control unit
14, 25 display unit
14a, 25a reference point
14b, 25b point
22 second sensor
50 operation instrument
60 operation table
880 pelvis
81 sacral bone
90 femur

BEST MODE FOR CARRYING OUT THE INVENTION

[First Embodiment of the Present Invention]

Now, an operation assisting system according to the first embodiment of the present invention will be described in detail below with reference to FIGS. 1 to 4.

In these respective figures, the operation assisting system 1 according to the first embodiment of the present invention comprises: three markers 10 that are provided on a surface of a body of a patient on a back side of a loin thereof, who is held in the decubitus position on an operation table 60, which is stationarily fixed during the operation, and have respective constant positional relationships; the first sensor 11 that is provided on the surface of the body of the patient so as to have constant positional relationship to the respective markers 10, to detect inclination of the first sensor 11 relative to a predetermined reference plane "A"; the third sensor 12 provided on the surface of the body of the patient at the femur region thereof to detect inclination of the third sensor 12 relative to the above-mentioned reference plane "A"; an arithmetic control unit 13 that is configured to receive outputs from the first sensor 11 and the third sensor 12, and determine, from the directions of the respective sensors, directions of the pelvis 80 and the femur 90 relative to the reference plane "A", to acquire an inclination angle in the inclination direction of the femur 90 relative to the pelvis 80; and a display unit 14 that is configured to generate instruction images indicative of the direction of the operation table 50 relative to the site of the body on which the operation is to be performed and deviation between a proper inclination of the pelvis 80 relative to the reference plane "A" and an actual inclination of the pelvis 80 relative thereto, and display the above-mentioned instruction images with these images changed.

The markers 10 are formed of a radiopaque material and provided at respective vertices of a triangle on the surface of the body of the patient on the back side of a sacral bone 81 of the pelvis 80 thereof. The above-mentioned surface of the body is placed in the vicinity of an acetabuli, on which the operation is to be performed, of the pelvis 80 of the patient, who is held in the decubitus position on an operation table 60, which is stationarily fixed during the operation. The surface of the body has a constant positional relationship to the pelvis 80. These markers have respective constant positional relationships to each other.

The first sensor 11, which is an inclination/position detection sensor provided based on an acceleration sensor, is configured to detect inclination of the first sensor 11 relative to the imaginary reference plane "A" (i.e., a plane extending perpendicularly to the upper surface of the operation table and in parallel with the longitudinal direction of the operation table), which is provided in a constant state relative to the operation table 60. The first sensor 11 is provided on the surface of the body of the patient on the back side of the sacral bone 81 thereof so as to be located substantially at a center of the triangle defined by the markers 10 to have the constant positional relationship to the respective markers 10 and the pelvis 80. The first sensor 11 acquires the positions of the pelvis 80 and the respective markers 10 by an X-ray photography applied before the operation and an accurate positional relationship to the pelvis 80, to detect inclination of the pelvis 80 from outputs of the sensor. Such a first sensor 11 is composed of a micro acceleration sensor and gel bodies between which the micro acceleration sensor is held so as to improve adhesion properties to the surface of the body and to be insusceptible to influence of vibration and impact from outside. In addition, the first sensor 11 has an extremely small size so as to prevent, when it is attached on the surface of the body of the patient or the operation instrument to detect inclination of the member, on which the sensor is attached, relative to the reference plane, the sensor from deteriorating the operability of the instrument or obstructing the operation.

An acceleration sensor as manufactured may be used as the first sensor 11 and the arithmetic control unit 13 may perform all the processing for signals outputted from the sensor. Alternatively, an A/D converting processor and/or a signal converting element may be combined together with an acceleration sensor into a united body serving as a unit for transmitting signals, which can be processed directly by a personal computer, provided that such a unit has a suitable size to be attached to the surface of the body of the patient. In this case, the personal computer may be used as the arithmetic control unit 13.

The third sensor 12 is attached to the surface of the femur region by means of a belt so as to have a constant positional relationship relative to the femur 90. This sensor has the same function as the first sensor 11 as described above. Description of the third sensor will therefore be omitted.

The arithmetic control unit 13 is connected to the first sensor 11 and the third sensor 12 as described above, as well as the display unit 14. The arithmetic control unit is configured to receive outputs from the first sensor 11 and the third sensor 12 as described above, acquire inclination of the pelvis 80 relative to the reference plane as described above from the inclination of the first sensor 11 as detected, and determine deviation between a proper inclination (a preset value) of the pelvis 80 relative to the reference plane, which the pelvis 80 should have during the operation to be performed on a site of the acetabuli of the pelvis 80, and an actual inclination of the pelvis 80 relative to the reference plane, to generate an instruction image indicative of the deviation. In addition, the arithmetic control unit 13 is also configured to acquire inclination of the femur 90 relative to the reference plane "A" to determine inclination of the femur 90 relative to the pelvis 80, and perform an arithmetic processing to obtain an bending angle of the joint.

The arithmetic control unit 13 acquires, during the operation, direction of the pelvis 80 of the patient relative to the reference plane "A", a position of which pelvis may be adjusted by an assistant for the operator on the operation table 60, and generates the instruction image indicative of how the actual inclination of the pelvis 80 deviates from the proper inclination so as to assist the assisting operation by the assistant.

The display unit 14 is disposed in a position where the operator and the assistant can observe in the operation space and any one of the operator and the assistant may not come into contact with the display unit during the operation. The display unit has the same display function as a conventional image display device utilizing a liquid crystal or a CRT and the description thereof will therefore be omitted. The display unit displays on its screen a reference point 14a indicative of a proper inclination of the pelvis 80 and a point 14b, which has been deviated from the proper inclination of the pelvis 80 and calculated based on the inclination of the pelvis 80 as actually measured.

Now, an operation assisting method using the operation assisting system according to the embodiment of the present invention will be described below. There is an assumption that the patient who have a hip replacement operation is held in the decubitus position on an operation table, with the side including the hip joint on which the operation is to be performed up so that a body axis extending from the head toward the legs is substantially in parallel with the longitudinal direction of the operation table. Prior to the operation, three markers 10 are attached to the surface of the body of the patient on the back side of the sacral bone of the pelvis 80 thereof so as to keep a constant positional relationship to the bone and a constant positional relationship between the three markers, the first sensor 11 is attached to the surface of the body at a center of the triangle defined by the three marker 10 so as to keep a constant positional relationship to the respective markers 10 and the first sensor 11 is connected to the arithmetic control unit 13 so as to enable outputs from the sensor to be input to the arithmetic control unit 13 (Step 101). Then, the entire of the pelvis including the markers 10 and the site on which the operation is to be performed is subjected to an X-ray photography to take X-rays of the pelvis in a plurality of directions (Step 102).

Inclination of the pelvis 80 relative to the reference plane "A" may be clearly recognized from X-ray images as taken, and the positional relationship between the respective markers and the pelvis 80 may simultaneously be recognized. In addition, the positional relationship between the pelvis 80 and the first sensor 11 may be clearly recognized from the constant positional relationship between the respective markers and the first sensor 11 on the surface of the body. Use of the positional relationship between the pelvis 80 and the first sensor 11 permits to calculate and acquire, from the inclination as detected by the sensor, an actual inclination of the pelvis 80 relative to the reference plane.

The inclination of the pelvis 80 relative to the reference plane "A", obtained through the X-ray photography is input as an initial information to the arithmetic control unit 13 (Step 103), and then the arithmetic control unit continues to receive outputs from the first sensor 11 to acquire movement of the pelvis 80 as variation of inclination. In addition, a proper inclination of the pelvis 80 relative to the reference plane "A", which the pelvis 80 should have during the operation, is also input as a target value to the arithmetic control unit 13 (Step 103), so as to permit to calculate deviation of the actual inclination of the pelvis from the above-mentioned proper inclination.

At this stage prior to the operation, in addition to the first sensor 11, the third sensor 12 may be attached, as an occasion demands, to a predetermined site of the femur region of the patient, and connected to the arithmetic control unit 13, so that the outputs from the sensors may be processed by the arithmetic control unit 13. An inclination angle of the femur 90 of the patient relative to the pelvis 80 thereof may be obtained by the arithmetic control unit 13. Use of such a configuration permits to store and accumulate in the arithmetic control unit 13 a critical angle of movement in the respective directions of the femur 90 relative to the pelvis 80, so as to provide a range of movement of the hip joint in accordance with the bending operation to be applied to the hip joint of the femur of the patient by a doctor, thereby providing a proper diagnosis and preparing an operation plan for a more appropriate progress of the operation.

Then, the arithmetic control unit 13 processes, during the operation, the outputs from the first sensor attached to the surface of the body of the patient to acquire successively inclination of the pelvis 80 relative to the reference plane "A" (Step 105). Then the arithmetic control unit 13 determines deviation between a proper inclination of the pelvis 80 of the patient, which the pelvis 80 should have during the operation on the basis of the operation plan as previously input, and an actual inclination of the pelvis 80 as detected by the first sensor 11 (Step 106) and then generates an image indicative of the deviation to input it to the display unit 14 (Step 107). The display unit 14 displays the image indicative of such a deviation (Step 108). The display unit 14 displays on its screen a reference point 14a indicative of the proper inclination of the pelvis as a reference point and a point 14b indicative of the direction and magnitude of the actual deviation. This makes it possible to recognize appropriately the state of the pelvis 80, which may change momentarily during the operation due to movement of the patient. Determination of the deviation by the arithmetic control unit 13 and display by the display unit 14 may be repeated until the operation is completed.

In a step of implanting an alternate acetabuli during the operation, an operator moves an operation instrument 50 to a position in the vicinity of the acetabuli of the pelvis 80, on which the operation is to be performed, in order to implant joint parts through the operation instrument 50. At this stage, the display unit 14 displays on its screen, as the point 14b placed apart from the reference point 14a, the state of deviation from the proper inclination of the pelvis 80, as determined in accordance with the processing of acquiring the inclination of the pelvis 80 relative to the reference plane "A" (see FIG. 8). During carrying out the operation in a state in which an operation cloth disables the operator from directly observing the entire hip of the patient, thus being difficult to confirm the direction of the pelvis 80, the operator directly moves the pelvis 80 to make a fine adjustment of the position of the pelvis so that the point 14b indicative of the deviation coincides with the reference point 14a, and namely so that the actual inclination of the pelvis 80 is the same as the proper inclination, which the pelvis 80 should have.

Then, the operator manipulates the operation instrument so as to direct it properly toward the acetabuli of the pelvis 80 in a normal manner carried out in case where the inclination of the pelvis 80 is kept to be coincident with the proper inclination thereof. An assistant holds the pelvis 80 in hands so as to keep a state in which the point 15b coincides with the reference point 14a on the screen of the display unit, and the operator manipulates the operation instrument in a predetermined direction for the acetabuli to set the operation instrument with the tip thereof directed to the target position in the predetermined direction. Then, the operator manipulates a striking member of the operation instrument 50 to apply a striking operation to the acetabuli to implant the joint parts in place of the acetabuli. Even when the pelvis unexpectedly moves to change its position during the operation, the instruction images on the screen of the display unit go along with this movement to change accordingly, with the result that the assistant may perform an appropriate operation to correct the position of the pelvis 80. Therefore, the operator may continue the steps of the operation, while preventing deviation of the operation instrument relative to the site on which the operation is to be performed.

In the operation as described above, the assistant moves the pelvis 80 so that the point 14b coincides with the reference point 14a on the screen of the display unit 14. The present invention is not limited only to such an embodiment. The operator may perform the operation so as to shift the operation instrument from the normal operation position of the operation instrument by a distance corresponding to the deviation of the pelvis 80.

The operation progresses and after the operator implants the joint parts into the respective sides of the pelvis and the femur and then connects these joint parts to each other so that the prosthetic joint becomes movable, the third sensor 12 may be attached, as an occasion demands, to the surface of the body of the patient at the femur thereof so as to keep a constant positional relationship to the femur 90 and connected to the arithmetic control unit 13 to which outputs from the third sensor 12 can be input. This enables the arithmetic control unit 13 to determine, in the middle of the operation, an angle of inclination of the femur 90 of the patient relative to the pelvis 80 thereof from the output of the first sensor 11 and the out put of the third sensor 12. Use of such a configuration permits to store and accumulate in the arithmetic control unit 13 a critical angle of movement in the respective directions of the femur 90 relative to the pelvis 80, so as to provide a range of movement of the hip joint after completion of the hip replacement, in accordance with the trial bending operation to be applied to the hip joint of the femur of the patient by the operator or the assistant, thereby providing a measure of the range of movement of the hip joint after the operation, and giving instructions on movement to the patient to prevent him or her from moving the prosthetic joint beyond the critical range of movement of thereof to cause dislocation or preparing a proper rehabilitation plan.

Further, after completion of the operation, the first sensor 11 may be attached, as an occasion demands, to the surface of the body of the patient on the back side of the pelvis 80 thereof, and the third sensor 12 is attached to the surface of the body of the patient at the femur region thereof and these sensors may be connected to the arithmetic control unit 13, thus enabling the arithmetic control unit 13 to determine from the outputs of the respective sensors an inclination angle of the femur 90 relative to the pelvis 80 after completion of the operation. Use of such a configuration permits to store and accumulate in the arithmetic control unit 13 a critical angle of movement in the respective directions of the femur 90 relative to the pelvis 80, so as to provide a range of movement of the hip joint after completion of the hip replacement, in accordance with the bending operation to be applied to the hip joint of the femur of the patient by the assistant, thereby providing the range of movement of the hip joint after the operation, and acknowledging properly a critical angle due to the other grounds than the specifications of the prosthetic joint to advance an effective rehabilitation program for the patient.

In addition, the display unit 14 may display, during a bending operation in the respective directions applied to the hip joint of the femur of the patient by the assistant, or based on the patient's will, the actual inclination angle of the femur 90 relative to the pelvis 80, together with the data of the range of movement of the hip joint, which has been accumulated through the actual measurement during the operation, thus permitting to give a clear visible indication of the range of movement to the assistant and/or the patient. Further, an annunciation unit may be used to perform annunciation that the femur has reached the critical angle on the basis of the data of the range of movement, thus permitting to inform the assistant or patient, who moves the femur of the critical angle of the prosthetic joint, to remind them of attention to dislocation or the other problems.

According to the operation assisting system of the embodiment of the present invention, the first sensor 11, which is capable of acquiring inclination thereof relative to the imaginary reference plane "A" kept in the fixed position, is provided on the surface of the body in the vicinity of the pelvis 80, with a positional relationship to the pelvis 80 kept constant, to acquire appropriately inclination of the pelvis 80 during the operation. This makes it possible to adjust the position of the pelvis 80 to an ideal state, when performing the operation in which the operation instrument must accurately reach the site of the pelvis 80 on which the operation is to be performed, and to handle always the operation instrument 50 by a certain operation as set to improve an operation accuracy, thus ensuring improvement in function of the site after completion of the operation. In addition, there is no need to an optical acquisition of three-dimensional position of the bone during the operation, thus solving difficulty in an appropriate positional measurement due to interception of the light for the positional measurement by the operator or assistant during the operation. There occur no problems that movement of the operator or assistant during the operation is limited by the positional measurement device, thus enabling the operator to concentrate upon performing the operation and providing an excellent operability.

[Second Embodiment of the Present Invention]

Figure 5:
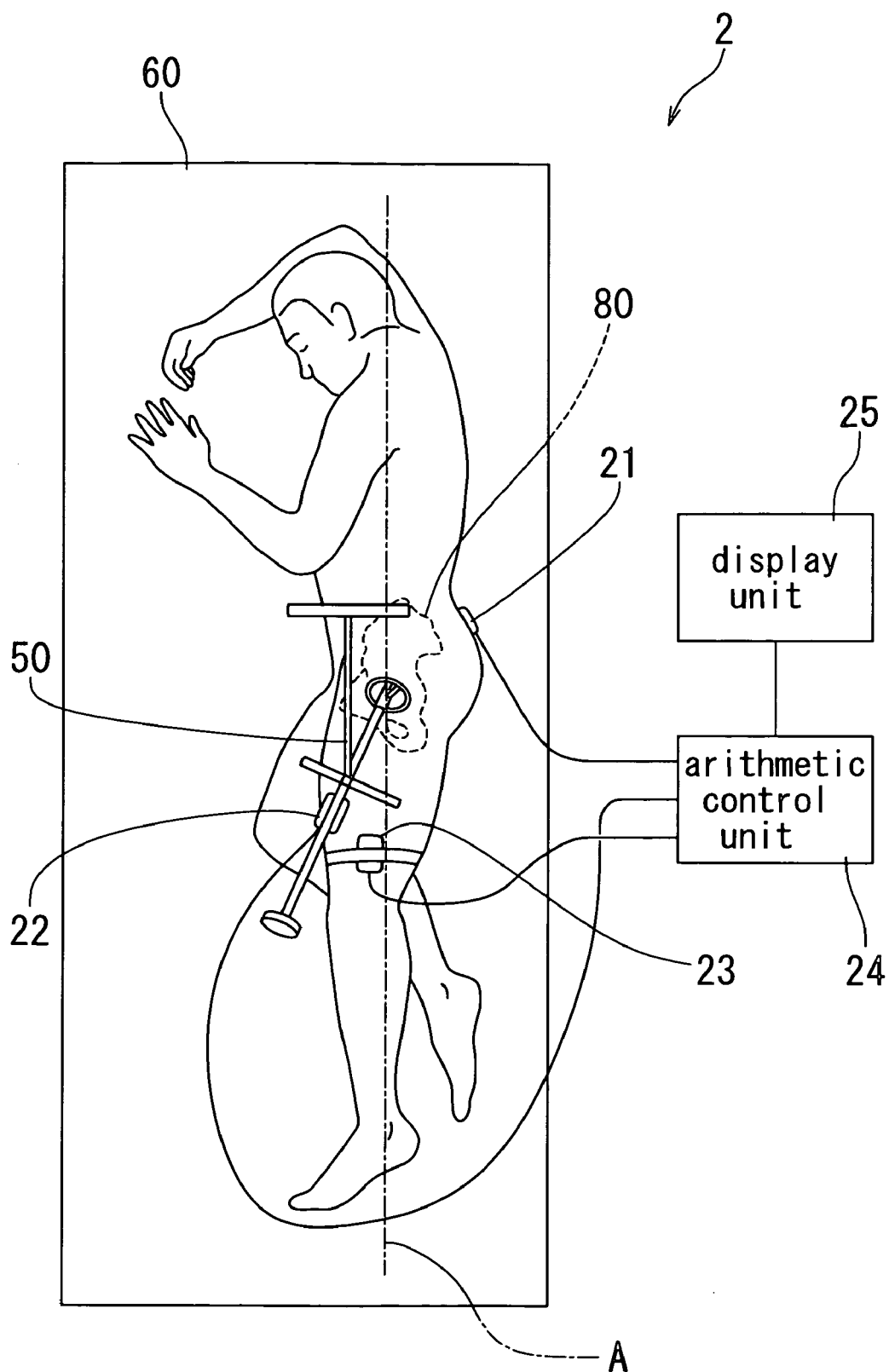
FIG. 5 is a schematic descriptive view of the operation assisting system according to the second embodiment of the present invention.
Figure 6:
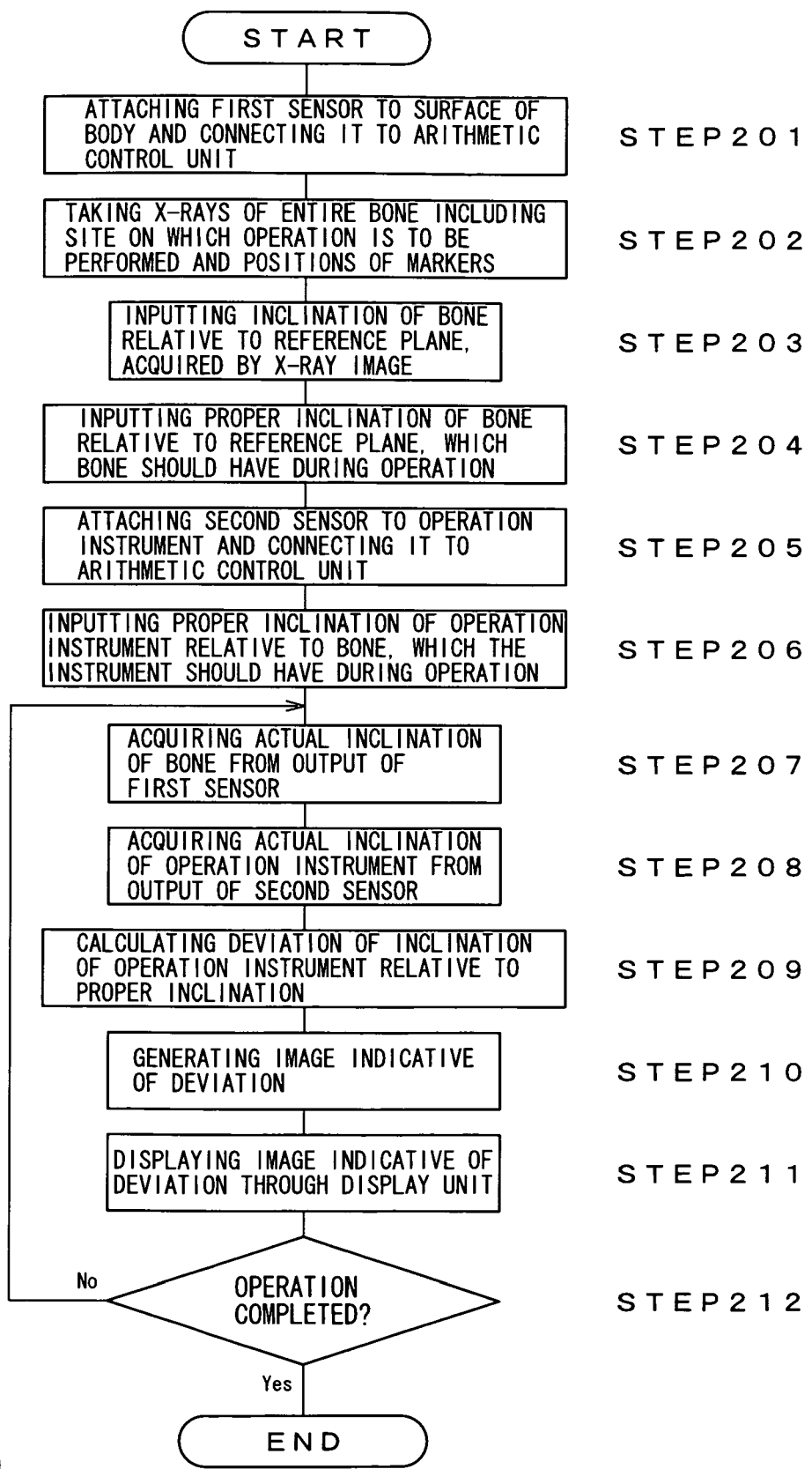
FIG. 6 is a flowchart of assisting operations in the operation assisting system according to the second embodiment of the present invention.
Figure 7:
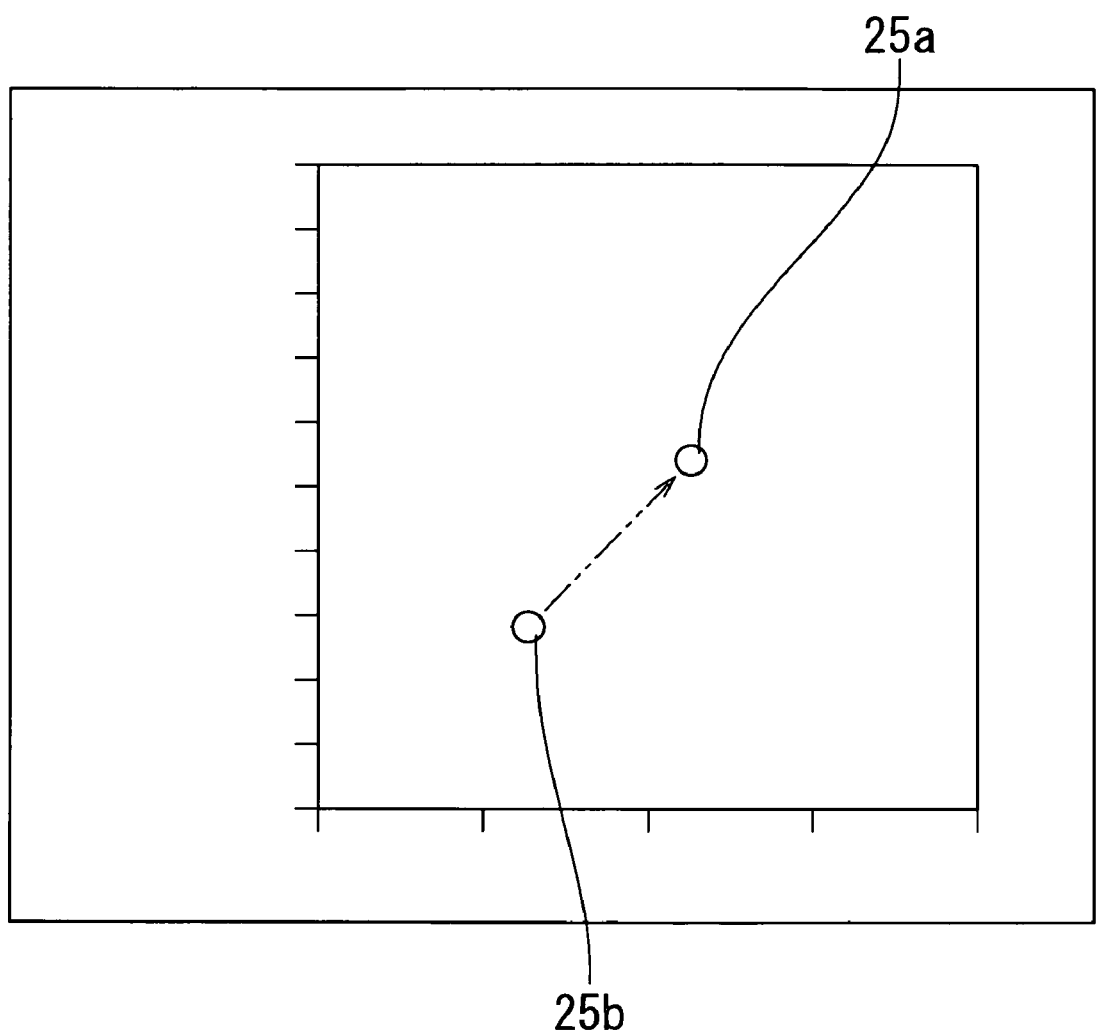
FIG. 7 is a descriptive view illustrating a screen of a display unit of the operation assisting system according to the second embodiment of the present invention.

Now, the operation assisting system according to the second embodiment of the present invention will be described in detail below with reference to FIGS. 5 to 7.

In these respective figures, the operation assisting system 2 according to the second embodiment of the present invention comprises, three markers 20, the first sensor 21, the third sensor 23, the arithmetic control unit 24, and the display unit 14 in the same manner as the first embodiment as described above of the present invention, and further comprises, unlike the first embodiment of the present invention, the second sensor 22 provided on the operation instrument at a predetermined position thereof to detect at least inclination of the operation instrument 50 relative to the reference plane "A" (i.e., the plane extending perpendicularly to the upper surface of the operation table and in parallel with the longitudinal direction of the operation table).

The second sensor 22 is attached to the operation instrument 50 at the predetermined position thereof. This second sensor is not attached to the surface of the body of the patient, and therefore has a configuration in which no gel bodies exist. The sensor has the same function as the first sensor 21 as described above and description of the second sensor will therefore be omitted.

The arithmetic control unit 24, which is connected to the first sensor 21 and the second sensor 22 as well as the display unit 25, is configured to receive outputs from the first sensor 21 and the second sensor 22 and acquire inclination of the pelvis 80 relative to the reference plane "A" based on the inclination as detected of the first sensor 21, and acquire inclination of the operation instrument 50 relative to the reference plane "A" based on the inclination as detected of the second sensor 22, to determine inclination of the operation instrument 50 relative to the pelvis 80, as well as determine deviation between a proper inclination (a preset value) of the operation instrument 50 relative to the pelvis 80, which the operation instrument 50 should have during the operation to be performed on the acetabuli of the pelvis 80, and an actual inclination of the operation instrument 50 relative to the pelvis 80, to generate an instruction image indicative of the deviation.

The arithmetic control unit 24 acquires from the inclination of the third sensor 22 the inclination of the femur 90 relative to the reference plane "A" and determines direction of the femur 90 relative to the pelvis 80, to perform processing to acquire an bending angle of the joint.

The arithmetic control unit 24 acquires, during the operation, direction of the operation instrument 50 manipulated by the operator, relative to the pelvis 80 and generates the instruction image indicative of how the actual inclination of the operation instrument 50 relative to the pelvis 80 deviates from the proper inclination which the operation instrument 50 should have, so as to assist the assisting operation by the assistant.

The display unit 25 is disposed in a position where the operator and the assistant can observe in the operation space and any one of the operator and the assistant may not come into contact with the display unit during the operation. The display unit has the same display function as the display unit of the first embodiment of the present invention as described above and the description thereof will therefore be omitted. The display unit displays on a portion of the screen thereof images indicative of deviation of the pelvis 80 from the proper inclination thereof and on the other portion of the screen thereof other images indicative of deviation of the operation instrument 50 from the proper inclination thereof. The images, which are displayed on the portion of the screen of the display unit and are indicative of the deviation of the pelvis from the proper inclination thereof, are the same as those of the first embodiment of the present invention as described above and the description thereof will therefore be omitted. The display unit displays on the other portion of the screen thereof a reference point 25a indicative of a proper inclination of the operation instrument 50 relative to the pelvis 80 and a point 25b, which has been calculated from the inclination of the operation instrument 50 as actually measured and is indicative of deviation from the proper inclination of the operation instrument 50.

Now, an operation assisting method using the operation assisting system according to the embodiment of the present invention will be described below. There is an assumption that the patient who have a hip replacement operation is held in the decubitus position on an operation table, with the side including the hip joint on which the operation is to be performed up so that a body axis extending from the head toward the legs, which is not subject to the operation is substantially in parallel with the longitudinal direction of the operation table. Prior to the operation, three markers 20 are attached to the surface of the body of the patient on the back side of the sacral bone of the pelvis 80 thereof, the first sensor 21 is attached to the surface of the body at a center of the triangle defined by the three marker 20 so as to keep a constant positional relationship to the respective markers 10 and the first sensor 21 is connected to the arithmetic control unit 24 (Step 201) in the same manner as the first embodiment of the present invention as described above. Then, the entire of the pelvis including the markers 20 and the site on which the operation is to be performed is subjected to an X-ray photography to take X-rays of the pelvis in a plurality of directions (Step 202).

Inclination of the pelvis 80 relative to the reference plane "A" may be clearly recognized from X-ray images as taken, and the positional relationship between the respective markers and the pelvis 80 may simultaneously be recognized. In addition, the positional relationship between the pelvis 80 and the first sensor 21 may be clearly recognized from the constant positional relationship between the respective markers 20 and the first sensor 21 on the surface of the body. Use of the positional relationship between the pelvis 80 and the first sensor 21 permits to calculate and acquire, from the inclination as detected by the sensor, an actual inclination of the pelvis 80 relative to the reference plane "A".

The inclination of the pelvis 80 relative to the reference plane "A", obtained through the X-ray photography is input as an initial information to the arithmetic control unit 23 (Step 203), and then the arithmetic control unit continues to receive outputs from the first sensor 21 to acquire movement of the pelvis 80 as variation of inclination. In addition, a proper inclination of the pelvis 80 relative to the reference plane "A", which the pelvis 80 should have during the operation, is also input as a target value to the arithmetic control unit 13 (Step 204), so as to permit to calculate deviation of the actual inclination of the pelvis from the above-mentioned proper inclination.

The second sensor 22 is attached to a predetermined position of the operation instrument 50, which serves as a tool to implant acetabuli joint parts, so as to keep a constant positional relationship to the operation instrument and is connected to the arithmetic control unit 24, so that the outputs from the sensor may be processed by the arithmetic control unit 24 (Step 205). A proper inclination of the operation instrument 50 relative to the pelvis 80 is also input as a target value to the arithmetic control unit 23 (Step 206).

The third sensor 23 may be attached, prior to the operation, to the surface of the body of the patient at the femur region thereof so as to keep a constant positional relationship to the femur 90 and may be connected to the arithmetic control unit 24 so as to enable the arithmetic control unit 24 to determine, from the outputs from the first sensor 21 and the outputs from the third sensor 23, an inclination angle of the femur 90 of the patient relative to the pelvis 80 thereof.

Then, the arithmetic control unit 24 processes, during the operation, the outputs from the first sensor 21 attached to the surface of the body of the patient to acquire successively inclination of the pelvis 80 relative to the reference plane "A" (Step 207). Then the arithmetic control unit 24 performs processing of the outputs from the second sensor 22 placed on the side of the operation instrument 50 to acquire inclination of the operation instrument 50 relative to the reference plane (Step 208). Then, the arithmetic control unit 24 determines deviation between a proper inclination of the operation instrument 50 relative to the pelvis 80, which the operation instrument should have during the operation on the basis of the operation plan as previously input, and an actual inclination of the operation instrument 50 as detected by the second sensor 22 (Step 209) and then generates an image indicative of the deviation to input it to the display unit 25 (Step 210). The display unit 25 displays the image indicative of such a deviation (Step 211). The display unit 14 displays on its screen a reference point 25a indicative of the proper inclination of the operation instrument 50 as a reference point and a point 25b indicative of the direction and magnitude of the actual deviation. This makes it possible to recognize appropriately a positional relationship between the pelvis 80, which may move momentarily during the operation due to movement of the patient, and the operation instrument 50, which may move momentarily during the operation due to its manipulation by the operator. Determination of the deviation by the arithmetic control unit 24 and display by the display unit 25 may be repeated until the operation is completed.

In addition, the arithmetic control unit 24 may determine deviation of the actual direction of the pelvis 80 acquired from the inclination as measured of the first sensor 21 relative to the proper inclination of the pelvis 80 of the patient, based on the information on the operation plan as previously input, generate an image indicative of such deviation (which includes the reference point indicative of the proper direction of the pelvis 80 and the point indicative of the direction and magnitude of the actual deviation, and cause the display unit to display the image on a portion of its screen or the other display unit to display the image, in the same manner as the first embodiment as described above of the present invention. This makes it possible to recognize appropriately the state of the pelvis 80, which may change momentarily during the operation due to movement of the patient.

In a step of implanting an alternate acetabuli during the operation, an operator moves an operation instrument 50 to a position in the vicinity of the acetabuli of the pelvis 80, on which the operation is to be performed, in order to implant joint parts through the operation instrument 50. At this stage, the display unit 25 displays on its screen, as the point 25b placed apart from the reference point 25a, the state of deviation from the proper inclination of the pelvis 80, as determined in accordance with the processing of acquiring a correlation of the pelvis 80 and the operation instrument 50 from the respective inclinations as acquired of the pelvis 80 and the operation instrument 50 relative to the reference plane "A" (see FIG. 7). During carrying out the operation in a state in which an operation cloth disables the operator from directly observing the entire hip of the patient, thus being difficult to confirm the direction of the pelvis 80, the operator may manipulate the operation instrument 50 in a normal manner carried out in case where the inclination of the pelvis 80 is kept to be coincident with the proper inclination thereof, while sometimes observing the screen of the display unit 25 to confirm as whether or not the operation instrument 50 is properly directed to the cite on which the operation is to be performed, and may carry out an operation as adjusted so as to cause the point 25*b* indicative of the deviation to coincide with the reference point 25*a*, and namely so that the actual direction of the operation instrument 50 is the same as the proper inclination.

The operator manipulates the operation instrument 50 in a predetermined direction to set the operation instrument with the tip thereof directed to the target position in the predetermined direction, while observing the screen of the display unit 25 and causing the point 25*b* indicative of the deviation to coincide with the reference point 25*a*. Then, the operator manipulates a striking member of the operation instrument 50 to apply a striking operation to the pelvis 80 to implant the joint parts in place of the acetabuli. Even when the pelvis unexpectedly moves to change its position during the operation, the instruction images on the screen of the display unit go along with this movement to change accordingly, with the result that the operator may perform an appropriate operation to correct the position of the pelvis 80. Therefore, the operator may continue the steps of the operation, while preventing deviation of the operation instrument relative to the site on which the operation is to be performed.

After completion of the step of implanting the prosthetic joint in the operation, the third sensor 23 may be attached, as an occasion demands, on the surface of the body of the patient at the femur region thereof so as to keep a constant positional relationship to the femur 90 and enable the arithmetic control unit 24 to process the outputs from the third sensor and to cause the display unit 25 to display the inclination angle of the pelvis 80 relative to the femur 90, in the same manner as the first embodiment as described above of the present invention.

According to the operation assisting system of the embodiment of the present invention, the second sensor 22 is provided on the operation instrument 50. This makes it possible to acquire, from the sensor input, inclination of the operation instrument 50 relative to the reference plane, cause the arithmetic control unit 24 to analyze the thus acquired inclination and the inclination of the pelvis 80 relative to the reference plane "A", which is outputted from the first sensor 21 provided on the side of the pelvis 80, to display deviation between the actual inclination of the operation instrument 50 and the proper inclination of the operation instrument 50 relative to the pelvis 80. Thus, the operator can manipulate the operation instrument 50 so as to reduce the deviation, while observing the display, to cause the operation instrument 50 to reach the site on which the operation is to be performed. An accurate operation can therefore be achieved through an appropriate guidance for the operation instrument in a simple mechanism, thus establishing a system for navigation of the operation at low costs.

Figure 8:
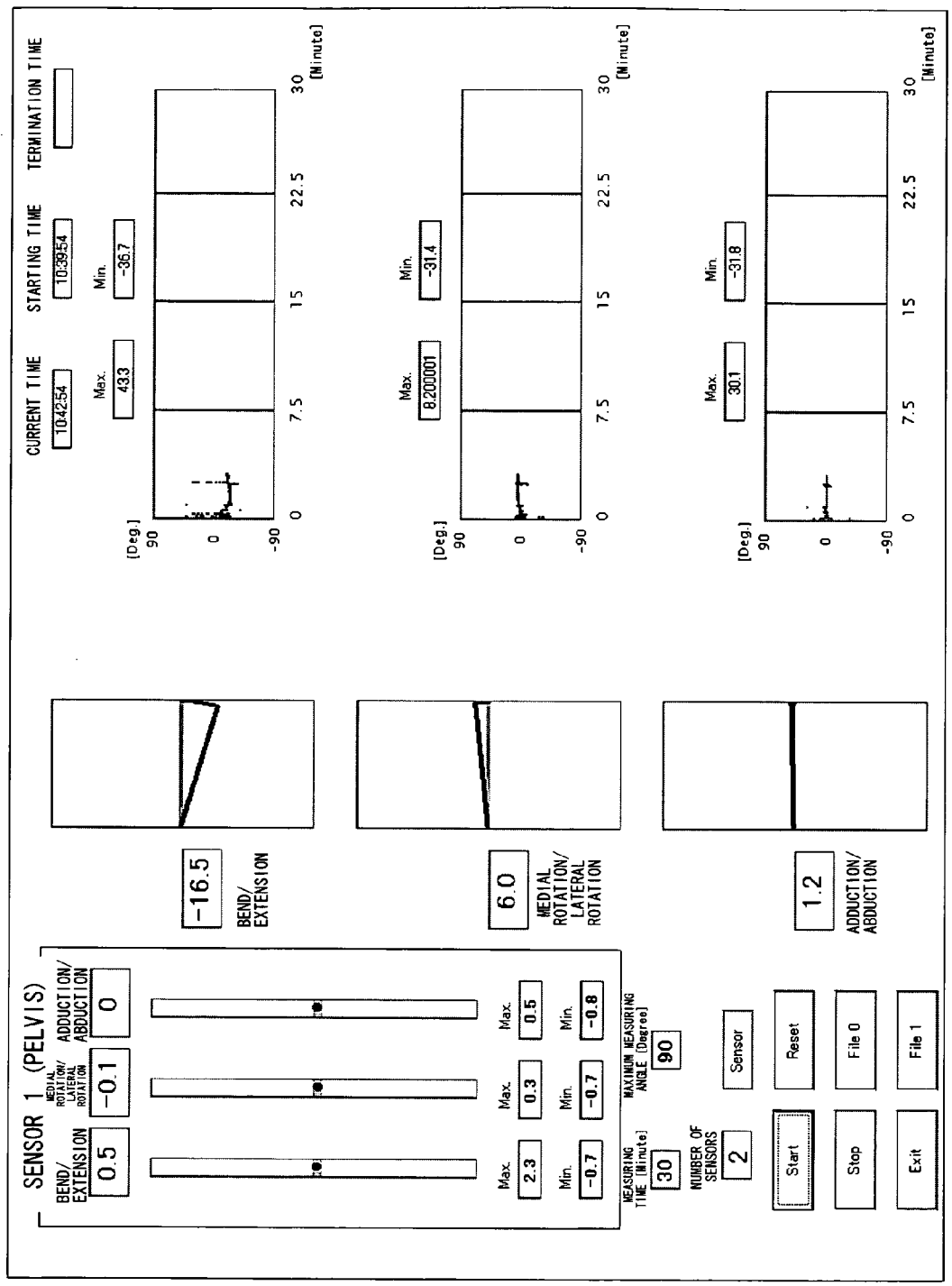
FIG. 8 is a descriptive view illustrating a screen of a display unit of the operation assisting system according to the other embodiment of the present invention.

In the operation assisting system according to the first and second embodiments as described above of the present invention, the display unit 14, 25 displays on the screen thereof two points, i.e., the reference point 14*a*, 25*a* and the point 14*b*, 25*b* indicative of the deviation, and there are carried out operations to adjust the inclination of the pelvis 80 and the direction of the operation instrument 50 so as to cause the point 14*b*, 25*b* indicative of the deviation to coincide with the reference point 14*a*, 25*a*. The present invention is not limited only to these embodiments. More specifically, a display unit as shown in FIG. 8 may for example be used to carry out the operation to adjust the inclination of the pelvis 80 and the direction of the operation instrument 50 in their proper states with the guidance utilizing the other form of instructions, such as numeric values and graphs. In the display unit of the operation assisting system as shown in FIG. 8, the left-hand and upper portion of the screen is an area to display an angle of rotation of the first sensor provided on the side of the pelvis in the respective directions of bend or extension; medial rotation or lateral rotation; and adduction or abduction, with a pointer-type indicator and numerical values. The operator may observe these angle indications to recognize instantaneously change in angle of the pelvis to carry out the adjustment operation. Three graphs displayed on the left side of the central portion of the screen show difference of angle in the above-mentioned three directions obtained from the first sensor attached to the pelvis and the second sensor attached to the operation instrument. These graphs may enable the operator to easily recognize the angles at the pelvis, thus performing an adjusting operation for the operation instrument. The right-hand side of the screen shows respective charts showing time-dependent change in difference of angles in the above-mentioned three directions. In addition to these features, a time-dependent change in angle of the pelvis and the femur obtained by the first sensor provided on the side of the pelvis and the third sensor provided on the femur may be determined to store and display the range of movement of the hip joint.

What is claimed is:

1. An operation assisting system, which comprises:
radiopaque markers (10, 20) provided at predetermined points on a surface of a body of a patient, who is to be held in a predetermined operational posture on an operating table (60) kept in a fixed position, said predetermined points being placed in a vicinity of a bone (80) of the patient, which is to be subjected to an operation, and having respective constant positional relationships relative to said bone (80), said radiopaque markers having constant positional relationships to each other;
a sensor (11, 21) provided at a predetermined point on the surface of the body of said patient so as to have a constant positional relationship relative to said markers (10, 20), said sensor being configured to detect at least inclination of the sensor relative to an imaginary reference plane (A), which is kept in a fixed position together with said operating table (60), said sensor enabling its positional relationship relative to the bone (80) to be acquired based on positional relationships between the bone (80) and the respective markers (10, 20), which have been previously acquired through an X-ray photography;
an arithmetic control unit (13, 24) configured to receive a sensor output from said sensor (11, 21) and acquire inclination of said bone (80) relative to said reference plane (A) based on the inclination as detected of the sensor (11, 21) and the positional relationship thereof relative to the bone (80), as well as determine deviation between a proper inclination of the bone (80) relative to said reference plane (A), which the bone (80) should have during the operation to be performed on a site of the bone, and an actual inclination of the bone (80) relative to said reference plane (A), to generate an instruction image indicative of the deviation; and
a display unit (14, 25) configured to display said instruction image.

2. The operation assisting system as claimed in claim 1, further comprising:
a second sensor (22) stationarily provided at a predetermined position on an operation instrument (50) to detect at least inclination of the second sensor relative to said reference plane (A), said operation instrument being placed in a vicinity of said site on which the operation is to be performed, and used through operation by an operator; and wherein:

said arithmetic control unit (24) is configured to receive a sensor output from said second sensor (22) and acquire inclination of said operation instrument (50) relative to said reference plane (A) based on the inclination as detected of the second sensor (22), as well as determine deviation between a proper inclination of the operation instrument (50) relative to said bone (80), which the operation instrument (50) should have during the operation to be performed on said site, and an actual inclination of the operation instrument (50) relative to said bone (80), to generate a second instruction image indicative of the deviation; and said display unit (25) or another display unit is configured to display said second instruction image.

3. The operation assisting system as claimed in claim 1, further comprising:

a third sensor (12, 23) provided at a predetermined point on the surface of the body, said predetermined point having a constant positional relationship relative to an other bone (90) adjacent to said bone (80) through a joint and placed in a vicinity of the other bone (90), to detect at least inclination of the third sensor relative to said reference plane (A); and wherein:

said arithmetic control unit (13, 24) is configured to receive a sensor output from said third sensor (12, 23) and acquire inclination of said other bone (90) relative to said reference plane (A) based on the inclination as detected of the third sensor (12, 23) to determine inclination of the other bone (90) relative to said bone (80), as well as receive, when an angle of the other bone (90) relative to said bone (80) in a predetermined inclination direction reaches a critical inclination angle, an angle value and the inclination direction, store said critical inclination angle in said inclination direction, accumulate the critical inclination angles in all of possible inclination directions and provide a range of movement of the joint to generate an image indicative of said range of movement; and said display unit (14, 25) or another display unit is configured to display said range of movement.

4. The operation assisting system as claimed in claim 2, further comprising:

a third sensor (12, 23) provided at a predetermined point on the surface of the body, said predetermined point having a constant positional relationship relative to an other bone (90) adjacent to said bone (80) through a joint and placed in a vicinity of the other bone (90), to detect at least inclination of the third sensor relative to said reference plane (A); and wherein:

said arithmetic control unit (13, 24) is configured to receive a sensor output from said third sensor (12, 23) and acquire inclination of said other bone (90) relative to said reference plane (A) based on the inclination as detected of the third sensor (12, 23) to determine inclination of the other bone (90) relative to said bone (80), as well as receive, when an angle of the other bone (90) relative to said bone (80) in a predetermined inclination direction reaches a critical inclination angle, an angle value and the inclination direction, store said critical inclination angle in said inclination direction, accumulate the critical inclination angles in all of possible inclination directions and provide a range of movement of the joint to generate an image indicative of said range of movement; and said display unit (14, 25) or another display unit is configured to display said range of movement.

5. The operation assisting system as claimed in claim 3, further comprising:

an input unit being configured to enable an operator to input an instruction to said arithmetic control unit (12, 24), said instruction being indicative that the inclination of said other bone (90) relative to said bone (80) reaches the critical inclination angle; and wherein:

said arithmetic control unit (13, 24) is configured to store, in case where, after prosthetic joint parts are fixed to the other bone (90) and said bone (90) to be subject to the operation and then the prosthetic joint parts are connected to each other, the inclination of said other bone (90) relative to said bone (80) due to a bending operation carried out by the operator or an operation assistant at a position of the joint of a body site including the other bone (90) of the patient reaches a critical angle of inclination without reaching a critical angle based on specifications of the prosthetic joint parts, said critical angle as the critical inclination angle in the predetermined inclination direction in accordance with an instruction input carried out thorough said input unit by the operator recognizing the critical angle of inclination as reached, as well as set, in an inclination direction at which a smooth inclination takes place to reach the critical angle based on the specifications of the prosthetic joint parts, the critical angle of the prosthetic joint parts as the critical inclination angle, accumulate the critical inclination angles in respective inclination directions and provide a range of movement of the joint between the other bone (90) and said bone (80) to generate an image indicative of said range of movement; and said display unit (14, 25) or another display unit is configured to display said range of movement.

6. The operation assisting system as claimed in claim 4, further comprising:

an input unit being configured to enable an operator to input an instruction to said arithmetic control unit (12, 24), said instruction being indicative that the inclination of said other bone (90) relative to said bone (80) reaches the critical inclination angle; and wherein:

said arithmetic control unit (13, 24) is configured to store, in case where, after prosthetic joint parts are fixed to the other bone (90) and said bone (90) to be subject to the operation and then the prosthetic joint parts are connected to each other, the inclination of said other bone (90) relative to said bone (80) due to a bending operation carried out by the operator or an operation assistant at a position of the joint of a body site including the other bone (90) of the patient reaches a critical angle of inclination without reaching a critical angle based on specifications of the prosthetic joint parts, said critical angle as the critical inclination angle in the predetermined inclination direction in accordance with an instruction input carried out thorough said input unit by the operator recognizing the critical angle of inclination as reached, as well as set, in an inclination direction at which a smooth inclination takes place to reach the critical angle based on the specifications of the prosthetic joint parts, the critical angle of the prosthetic joint parts as the critical inclination angle, accumulate the critical inclination angles in respective inclination directions and provide a range of movement of the joint between the other bone (90) and said bone (80) to generate an image indicative of said range of movement; and said display unit (14, 25) or another display unit is configured to display said range of movement.

7. The operation assisting system as claimed in claim 3, wherein:

said arithmetic control unit (13, 24) is configured to output a predetermined annunciation signal, in case where the inclination of said other bone (90) relative to said bone (80) in the predetermined inclination direction due to a bending operation carried out after completion of the operation by an assistant at a position of the joint of a body site including the other bone (90) of the patient, or due to a moving action of the patient based on his/her will, reaches a critical angle of inclination in said inclination direction, which has been derived from known data of the range of movement for the prosthetic joint parts as implanted; and said system further comprising:

an annunciation unit being configured to receive said annunciation signal and perform annunciation relative to said assistant and/or the patient.

8. The operation assisting system as claimed in claim 4, wherein:

said arithmetic control unit (13, 24) is configured to output a predetermined annunciation signal, in case where the inclination of said other bone (90) relative to said bone (80) in the predetermined inclination direction due to a bending operation carried out after completion of the operation by an assistant at a position of the joint of a body site including the other bone (90) of the patient, or due to a moving action of the patient based on his/her will, reaches a critical angle of inclination in said inclination direction, which has been derived from known data of the range of movement for the prosthetic joint parts as implanted; and said system further comprising:

an annunciation unit being configured to receive said annunciation signal and perform annunciation relative to said assistant and/or the patient.

9. The operation assisting system as claimed in claim 5, wherein:

said arithmetic control unit (13, 24) is configured to output a predetermined annunciation signal, in case where the inclination of said other bone (90) relative to said bone (80) in the predetermined inclination direction due to a bending operation carried out after completion of the operation by an assistant at a position of the joint of a body site including the other bone (90) of the patient, or due to a moving action of the patient based on his/her will, reaches a critical angle of inclination in said inclination direction, which has been derived from known data of the range of movement for the prosthetic joint parts as implanted; and said system further comprising:

an annunciation unit being configured to receive said annunciation signal and perform annunciation relative to said assistant and/or the patient.

10. The operation assisting system as claimed in claim 6, wherein:

said arithmetic control unit (13, 24) is configured to output a predetermined annunciation signal, in case where the inclination of said other bone (90) relative to said bone (80) in the predetermined inclination direction due to a bending operation carried out after completion of the operation by an assistant at a position of the joint of a body site including the other bone (90) of the patient, or due to a moving action of the patient based on his/her will, reaches a critical angle of inclination in said inclination direction, which has been derived from known data of the range of movement for the prosthetic joint parts as implanted; and said system further comprising:

an annunciation unit being configured to receive said annunciation signal and perform annunciation relative to said assistant and/or the patient.

11. The operation assisting system as claimed in claim 1, wherein:

said bone (80) comprises a pelvis;

said markers (10, 20) are provided at respective vertices of a triangle on the surface of the body of the patient on a back side of a sacral bone (81) of the pelvis; and said sensor (11, 21) is provided within the triangle including the markers (10, 20) at the vertices thereof on the back side of the sacral bone (81) of the pelvis.

12. The operation assisting system as claimed in claim 2, wherein:

said bone (80) comprises a pelvis;

said markers (10, 20) are provided at respective vertices of a triangle on the surface of the body of the patient on a back side of a sacral bone (81) of the pelvis; and said sensor (11, 21) is provided within the triangle including the markers (10, 20) at the vertices thereof on the back side of the sacral bone (81) of the pelvis.

13. The operation assisting system as claimed in claim 3, wherein:

said bone (80) comprises a pelvis;

said markers (10, 20) are provided at respective vertices of a triangle on the surface of the body of the patient on a back side of a sacral bone (81) of the pelvis; and said sensor (11, 21) is provided within the triangle including the markers (10, 20) at the vertices thereof on the back side of the sacral bone (81) of the pelvis.

14. The operation assisting system as claimed in claim 4, wherein:

said bone (80) comprises a pelvis;

said markers (10, 20) are provided at respective vertices of a triangle on the surface of the body of the patient on a back side of a sacral bone (81) of the pelvis; and said sensor (11, 21) is provided within the triangle including the markers (10, 20) at the vertices thereof on the back side of the sacral bone (81) of the pelvis.

15. The operation assisting system as claimed in claim 5, wherein:

said bone (80) comprises a pelvis;

said markers (10, 20) are provided at respective vertices of a triangle on the surface of the body of the patient on a back side of a sacral bone (81) of the pelvis; and said sensor (11, 21) is provided within the triangle including the markers (10, 20) at the vertices thereof on the back side of the sacral bone (81) of the pelvis.

16. The operation assisting system as claimed in claim 6, wherein:

said bone (80) comprises a pelvis;

said markers (10, 20) are provided at respective vertices of a triangle on the surface of the body of the patient on a back side of a sacral bone (81) of the pelvis; and said sensor (11, 21) is provided within the triangle including the markers (10, 20) at the vertices thereof on the back side of the sacral bone (81) of the pelvis.

17. The operation assisting system as claimed in claim 7, wherein:
   said bone (80) comprises a pelvis;
   said markers (10, 20) are provided at respective vertices of a triangle on the surface of the body of the patient on a back side of a sacral bone (81) of the pelvis; and
   said sensor (11, 21) is provided within the triangle including the markers (10, 20) at the vertices thereof on the back side of the sacral bone (81) of the pelvis.

18. The operation assisting system as claimed in claim 8, wherein:
   said bone (80) comprises a pelvis;
   said markers (10, 20) are provided at respective vertices of a triangle on the surface of the body of the patient on a back side of a sacral bone (81) of the pelvis; and
   said sensor (11, 21) is provided within the triangle including the markers (10, 20) at the vertices thereof on the back side of the sacral bone (81) of the pelvis.

19. The operation assisting system as claimed in claim 9, wherein:
   said bone (80) comprises a pelvis;
   said markers (10, 20) are provided at respective vertices of a triangle on the surface of the body of the patient on a back side of a sacral bone (81) of the pelvis; and
   said sensor (11, 21) is provided within the triangle including the markers (10, 20) at the vertices thereof on the back side of the sacral bone (81) of the pelvis.

20. The operation assisting system as claimed in claim 10, wherein:
   said bone (80) comprises a pelvis;
   said markers (10, 20) are provided at respective vertices of a triangle on the surface of the body of the patient on a back side of a sacral bone (81) of the pelvis; and
   said sensor (11, 21) is provided within the triangle including the markers (10, 20) at the vertices thereof on the back side of the sacral bone (81) of the pelvis.

* * * * *